United States Patent [19]

Mantovani et al.

[11] 4,334,101
[45] Jun. 8, 1982

[54] METHOD FOR PREPARING METAL-CARBONYL CLUSTERS IMMOBILIZED IN ZEOLITE AND THEIR USE AS HETEROGENEOUS CATALYSTS

[75] Inventors: Elvio Mantovani; Nicola Palladino; Antonio Zanobi, all of Rome, Italy

[73] Assignee: Snamprogetti S.p.A., Milan, Italy

[21] Appl. No.: 86,350

[22] Filed: Oct. 19, 1979

Related U.S. Application Data

[62] Division of Ser. No. 874,196, Feb. 1, 1978, Pat. No. 4,199,478.

[30] Foreign Application Priority Data

Feb. 1, 1977 [IT] Italy ............................. 19833 A/77

[51] Int. Cl.³ .................. C07C 45/50; C07C 47/00
[52] U.S. Cl. .................................. 568/454; 568/451; 568/882; 568/909; 252/455 Z
[58] Field of Search .............. 568/454, 909, 451, 453, 568/882; 260/604; 252/455 Z

[56] References Cited

U.S. PATENT DOCUMENTS

| | | | |
|---|---|---|---|
| 3,880,937 | 4/1975 | Massie | 568/909 |
| 3,940,447 | 2/1976 | Yoo | 568/909 |
| 3,954,883 | 5/1976 | Haag et al. | 568/909 |
| 3,980,583 | 9/1976 | Mitchell et al. | 568/909 |
| 4,070,403 | 1/1978 | Homeier | 568/909 |
| 4,197,414 | 4/1980 | Hartwell et al. | 568/909 |

*Primary Examiner*—Werren B. Lone
*Attorney, Agent, or Firm*—Morgan, Finnegan, Pine, Foley and Lee

[57] ABSTRACT

Metal carbonyl clusters occluded in zeolites are prepared, to be used as catalyst in certain special reactions such as hydroformylation of diene hydrocarbons.

Rhodium complexes are immobilized in certain zeolites and the catalyst thus obtained can be used as a heterogeneous catalyst.

2 Claims, No Drawings

METHOD FOR PREPARING METAL-CARBONYL CLUSTERS IMMOBILIZED IN ZEOLITE AND THEIR USE AS HETEROGENEOUS CATALYSTS

This is a division of application Ser. No. 874,196 filed Feb. 1, 1978, now U.S. Pat. No. 4,199,478.

This invention relates to a method for preparing carbonyl clusters of transition metals, and their use as heterogeneous catalysts.

The use of metal-carbonyls as homogeneous catalysts is very extensive, but their preparation often requires drastic reaction conditions, especially when starting directly from the metal, and, during progress of the catalytic reactions which occur in a homogeneous phase, their recovery is a problem, both for reasons of economy and prevention of pollution.

It is known that in a case where a very high degree of dispersion of the metal is obtained, the temperature and pressure conditions required for preparing the corresponding metal-carbonyls therefrom are blander; the problem of recovery and recycling of a homogeneous catalyst is likewise known, such problem being obviated by making the catalyst heterogeneous. In the case of the metal carbonyls prepared, according to the present method, with zeolites, both problems mentioned above can be obviated. As a matter of fact, the immobilization of the metal in the zeolite acts in such a way that, when the metal is reduced, it remains an extremely fine dispersed state so that the preparation conditions for making the corresponding carbonyl clusters become particularly bland. Moreover, since the cluster is immobilized in the interior of the crystalline structure of the zeolite, such a cluster cannot be dissolved as it is used as a catalyst, and can thus be easily recovered and recycled as well.

The use of the zeolites as a supporting body can in part to the immobilized catalyst properties of selectivity and activity that the catalyst does not possess when used in a homogeneous phase.

The selected metal is bound in the interior of the crystalline structure between the zeolite by exchange of the zeolite are a solution of the metal in the form of a complex salt or ion.

For exchanged or bound metal is then reduced and carbonylated in situ, the result being the formation of carbonyl clusters.

Generally speaking, any zeolite which has hollow spaces of the appropriate size in the crystalline structure can conveniently be used as a support within which, according to the method disclosed herein, metal carbonyl clusters and, more particularly carbonyls of metals of the VIII Group of the Periodic Table, can be synthesized. In the zeolites in which the hollow spaces are interconnected by channels having a size less than that of the metal clusters which have been synthesized in their interior, such clusters remain occluded in the crystalline structure of the zeolite and make the release of the catalyst in the reaction mixture virtually impossible. The size of the hollow spaces and the channels which interconnect them, the zeolites of the X and Y types are those which lend themselves quite preferentially for use as supporting bodies due to the size of their hollow spaces and the channels which inconnect them. As a matter of fact, the zeolites of the faujazite type, to which the X and Y zeolites belong, possess a structure in which three types of hollow spaces are present, these being formed by tetrahedra of $SiO_4$ and $AlO_4$.

Of these, the largest of the hollow spaces, which are called the supercages, have a diameter of about 13 angstrom units and are mutually connected by channels of 8-9 angstrom units, whereas the smallest of the hollow spaces have a diameter of less than 7 angstrom units.

The carbonyl clusters are synthesized in situ in the supercages according to the method of the present invention and remain trapped in the zeolite since their dimensions do not match the zeolite channels, thus the clusters remain available for catalytic reactions in those cases in which the substrate, because of its dimensions, can have an access thereto.

A method which is particularly appropriate for preparing such carbonyl clusters is that of exchanging the zeolite with complex compounds of the type $[Me(NH_3)_a]X_b$ in which Me is a metal of the Eighth Group of the Periodic Table, X is a halogen, a varies from 4 to 6 consistently with the valenced the metal concerned, and b is equal to the oxidation number of the metal. The thusly so exchanged zeolite is treated with a mixture of $H_2$ and CO at a pressure and a temperature which are appropriately selected each time according to the metal present in the complex compound. A confirmation of the completion of the formation of the carbonyl clusters is obtained by Infra Red spectroscopy, by investigating the strip 2,100–1,800 $cm^{-1}$ which is typical of the coordinated carbonyls. The final contents of the metal carbonyl in the zeolite can appropriately be varied by adjusting the intensity of the exchange.

A particular interest from the economic standpoint is the fact that there is no loss of metal during the process of the exchange or the reduction. After the preparation of the metal-carbonyl cluster in the zeolite, the latter, after having been washed and dried, is stored without any special precautions for long periods of time without any evidence of decomposition of the occluded complex.

The metal-carbonyl clusters prepared in this way retain their catalytic properties and their use is particularly recommended for hydroformylation reactions of olefins, such as illustrated in the Examples which follow, in the synthesis of esters of carboxylic acids from olefins, alcohols and carbon monoxide, and in cyclization reactions of acetylene to form aromatic compounds.

Although the catalysts so formed are preferred for use in reactions in the liquid phase, they can be used also for reactions carried out in the gaseous phase.

The invention is illustrated by the following Examples.

EXAMPLE 1

Na Y zeolite 3 grams is exchanged with rhodium by exchanging the zeolite so that it becomes balanced with 80 milligrams of the complex $[Rh(NH_3)_6]Cl_3$, as prepared according to the standard conventional methods, dissolved in 50 mls of water. After about 48 hrs the UV-spectrum of the solution indicates the discharge of the complex from the solution and the analysis of the chloride ions therein indicates that the exchange has taken place. The exchanged zeolite is then washed with water until the chloride ions are no longer detectable, dried and the presence in the zeolite interior of the rhodium aminic complex is confirmed through the identification in the Infrared spectrum of a band at 1322 $cm^{-1}$, which is characteristic for such a complex. The thusly exchanged zeolite is then treated in an autoclave for 48 hours at 130° C. with a mixture of CO and $H_2$ (1:1)

under a pressure of 80 atm, the result being a product which is intensely colored red and the analysis of which indicates a rhodium content of 1%. The Infrared spectrum exhibits the discharge of the band at 1322 cm$^{-1}$ which is characteristic of the rhodium aminic complex, and the appearance on intense bands at 2095, 2080 (sh), 2060 and 1765 cm$^{-1}$, which indicate the presence of coordinated carbon monoxide and the formation in the zeolite of rhodium carbonyl clusters.

The thusly prepared catalyst is used in the hydroformylation of hexene-1. 71 milligrams of catalyst ($7 \times 10^{-3}$ milligram atoms of Rhodium) and 1 ml of hexene-1 in 5 mls hexane, are placed in an autoclave having a volume of 200 mls which is charged with a mixture of CO and H$_2$ (1:1) under a pressure of 80 atm and brought to 80° C. After 8 hours, the autoclave is brought to room temperature and the reactionn mixture is analyzed by gaschromotography. The conversion of hexene-1 into aldehyde is about 98%, of which 51% is heptanal, 41% is 2-methyl-hexanal, and 8% is 2-ethyl-pentanal. Other products of the reaction are present in amounts of less than 1%.

EXAMPLES 2 TO 9

The catalyst of Example 1 is recovered by filtration of the reaction mixture and reused, under the same conditions, in 8 subsequent tests involving hydroformylation (see Tables 1 and 2). Test No. 8 gives the same results with respect to conversion values and composition of the reaction mixture as reported in Example 1 above and shows the high stability of the catalyst which retains its properties unaltered even after a member of repeated catalytic cycles.

The loss of catalyst during the reaction is extremely low and, as a matter of fact, the average content of rhodium in the reaction mixture, as analyzed by atomic absorption, was about 3 parts per million.

TABLE 1

Working conditions: pressure 80 atm (CO + 1 H$_2$)
5 mls hexane: 1 ml hexene-1
71 milligrams of catalyst ($7 \times 10^{-3}$ milligram atoms of Rh)

| Test No. | Temp. °C. | % heptanal | % 2 methyl-hexanal | % 2-ethyl-pentanal | n/i (°) | Conversion of the starting olefin, % |
|---|---|---|---|---|---|---|
| 1 | 50 | 56 | 45 | — | 1.2 | 10 |
| 2 | 83 | 51 | 41 | 8 | 1.0 | 95 |
| 3 | 100 | 49 | 36 | 15 | 1.0 | 95 |
| 4 | 130 | 41 | 45 | 14 | 0.7 | 95 |

(°) n/i = ratio of normal aldehyde to the isoaldehyde

TABLE 2

Working conditions: temperature 80° C. - 5 mls hexane - 1 ml Hexene-1 71 milligrams of catalyst ($7.10^{-3}$ milligram-atoms of Rh)

| Test No | Pressure of the mixture (1CO + 1H$_2$) atm. | % heptanal | % 2-methyl hexanal | % 2-ethyl pentanal | n/i (°) | Conversion of the starting olefin, % |
|---|---|---|---|---|---|---|
| 5 | 30 | — | — | — | — | — |
| 6 | 50 | 43 | 46 | 11 | 0.8 | 80 |
| 7 | 100 | 52 | 40 | 8 | 1.1 | 95 |
| 8 | 80 | 51 | 41 | 8 | 1.0 | 95 | n/i = ratio of normal aldehyde to the isoaldehyde

EXAMPLE 10

71 milligrams of catalyst ($7.10^{-3}$ milligram atoms of rhodium) prepared as in Example 1 and 1 ml of 1,5-hexadiene in 5 mls benzene are placed in a 200-ml autoclave which is charged at 80 atm with a mixture of CO and H$_2$ (1:1) and brought to 80° C. After 8 hours the autoclave is restored to room temperature and the reaction mixture analyzed by gaschromatography.

The conversion of 1,5-hexadiene is higher than 80%, 41% of which is monoaldehyde and 51% are four isomers of dialdehydes in the respective percentages of 42%, 8%, 6% and 3%.

We claim:

1. The use as heterogeneous catalysts in hydroformylation reactions of olefins and dienes, of metal carbonyl clusters trapped in the interior of the crystalline structure of zeolites, prepared by exchanging a zeolite with a metal in the form of a salt or an ion complex, subsequently reducing and carbonylating the metal itself, forming metal carbonyl clusters in the interior of said zeolite, hydroformylating an olefin or a diene under a pressure in a range of from about 50 to about 100 atmospheres, at a temperature in a range of from about 80° C. to about 130° C. in the presence of said zeolite having said metal carbonyl clusters trapped in the interior thereof and recovering aldehyde.

2. The use as heterogeneous catalysts in hydroformylation reactions of olefins and dienes, of zeolites of the types X and Y which contain rhodium carbonyl clusters trapped in the interior structure of the zeolites and which are prepared by exchanging a zeolite with an aqueous solution of [Rh(NH$_3$)$_6$]Cl$_3$ and forming a zeolite having a rhodium aminic complex trapped in the interior of the crystalline structure of the zeolite, reducing and carbonylating the exchanged zeolite with a mixture of CO and H$_2$ and forming rhodium carbonyl clusters in the interior of said zeolite; hydroformylating an olefin or a diene under a pressure in a range of from about 50 to about 100 atmospheres, at a temperature in a range of from about 80° C. to about 130° C. in the presence of said zeolite having said rhodium carbonyl clusters trapped in the interior thereof and recovering aldehyde.

* * * * *